(12) United States Patent
McGregor

(10) Patent No.: US 10,500,089 B2
(45) Date of Patent: Dec. 10, 2019

(54) CONVECTIVE DEVICE WITH FLOW CONTROL DEVICE AND MULTIPLE INFLATABLE SECTIONS

(71) Applicant: 3M INNOVATIVE PROPERTIES COMPANY, St. Paul, MN (US)

(72) Inventor: Andrew J. McGregor, Minneapolis, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 734 days.

(21) Appl. No.: 15/039,540

(22) PCT Filed: Dec. 2, 2014

(86) PCT No.: PCT/US2014/068126
§ 371 (c)(1),
(2) Date: May 26, 2016

(87) PCT Pub. No.: WO2015/084827
PCT Pub. Date: Jun. 11, 2015

(65) Prior Publication Data
US 2017/0027743 A1    Feb. 2, 2017

Related U.S. Application Data

(60) Provisional application No. 61/912,829, filed on Dec. 6, 2013.

(51) Int. Cl.
*A61F 7/02* (2006.01)
*A61F 7/00* (2006.01)

(52) U.S. Cl.
CPC .......... *A61F 7/02* (2013.01); *A61F 2007/006* (2013.01); *A61F 2007/0091* (2013.01); *A61F 2007/0268* (2013.01)

(58) Field of Classification Search
None
See application file for complete search history.

(56) References Cited

U.S. PATENT DOCUMENTS

| 3,712,288 A | 1/1973 | Weiss |
| 6,524,332 B1 | 2/2003 | Augustine |

(Continued)

FOREIGN PATENT DOCUMENTS

| DE | 20006960 | 12/2000 |
| DE | 202012103044 | 1/2014 |

(Continued)

OTHER PUBLICATIONS

Machine Translation of FR2729746 A1 to Zaniewski, Michael (Year: 1996).*

(Continued)

*Primary Examiner* — Kaitlyn E Smith
(74) *Attorney, Agent, or Firm* — 3M Innovative Properties Company; Jonathan V. Sry

(57) ABSTRACT

At least some aspects of the present disclose feature a flow control device to be used between two inflatable sections. The flow control device is a one-way flow control device allowing inflating medium to flow in one direction. In such embodiments, the flow control device is in an open state when a first inflatable section is inflated such that a second inflatable section is also inflated. The flow control device is in close state when the second inflatable section is inflated such that the first inflatable section is not inflated.

15 Claims, 7 Drawing Sheets

(56) References Cited

U.S. PATENT DOCUMENTS

| | | |
|---|---|---|
| 6,876,884 B2 | 4/2005 | Hansen |
| 7,276,076 B2 | 10/2007 | Bieberich |
| 7,520,889 B2 | 4/2009 | Van Duren |
| 7,749,261 B2 | 7/2010 | Hansen |
| 7,819,911 B2 | 10/2010 | Anderson |
| 7,871,428 B2 | 1/2011 | Augustine |
| 7,976,572 B2 | 7/2011 | Ziaimehr |
| 2003/0195596 A1 | 10/2003 | Augustine |
| 2005/0015127 A1 | 1/2005 | Bieberich |
| 2006/0259104 A1* | 11/2006 | Panser .................. A61F 7/00 607/104 |
| 2011/0066215 A1 | 3/2011 | Panser |

FOREIGN PATENT DOCUMENTS

| | | |
|---|---|---|
| FR | 2729746 | 7/1996 |
| WO | WO 2003-086500 | 10/2003 |
| WO | WO 2014/158463 | 10/2014 |

OTHER PUBLICATIONS

International Search Report for PCT International Application No. PCT/US2014/068126, dated May 8, 2015, 6 pages.

* cited by examiner

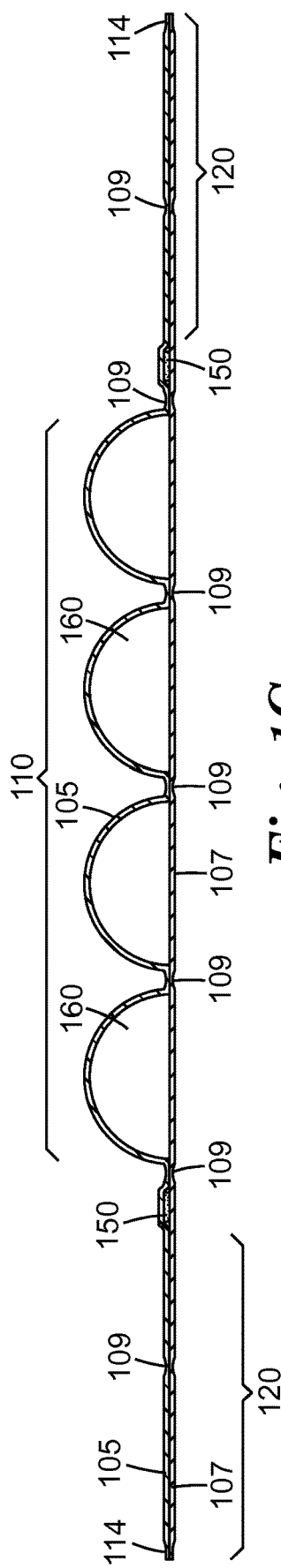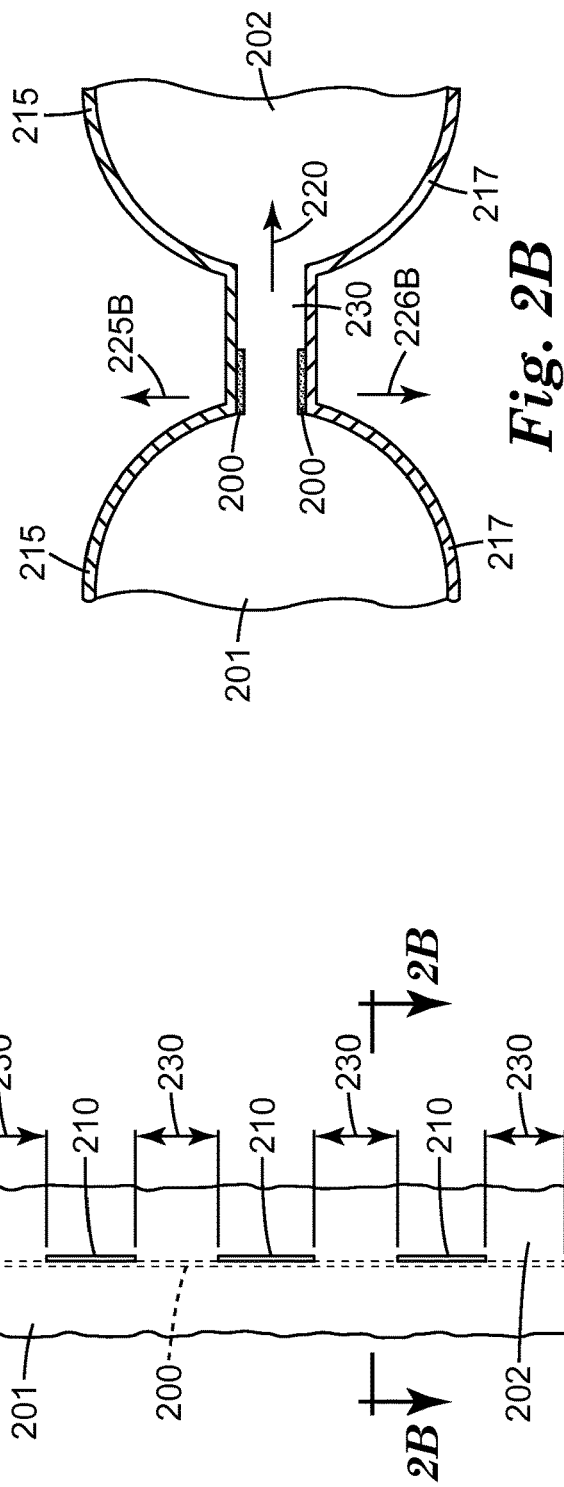

100 mmHg,
CONVECTIVE DEVICE WITH FLOW CONTROL DEVICE AND MULTIPLE INFLATABLE SECTIONS

TECHNICAL FIELD

The present disclosure relates generally to convective devices with more than one inflatable section.

SUMMARY

At least some aspects of the present disclosure feature a convective device including a first inflatable section having a first opening, a second inflatable section having a second opening, and a flow control device disposed between the first inflatable section and the second inflatable section. The flow control device is configured to open when the second inflatable section is inflated with inflating medium. The flow control device is configured to remain closed when the first inflatable section is inflated with inflating medium.

At least some aspects of the present disclosure feature a flow control device including an air permeable strip and an air impermeable strip. The air permeable strip has a first side, a second side, a first end, and a second end. The air impermeable strip has a first side, a second side, a first end, and a second end. The second side of the air impermeable strip is proximate the second side of the air permeable strip. The air impermeable strip is configured to cover the air permeable strip in a close state of the flow control device and uncover the air permeable strip in a open state of the flow control device.

BRIEF DESCRIPTION OF THE DRAWINGS

The accompanying drawings are incorporated in and constitute a part of this specification and, together with the description, explain the advantages and principles of the invention. In the drawings.

FIG. 1C is a cross sectional view of the embodiment illustrated in FIG. 1A;

FIG. 2A is a top view of one embodiment of a flow control device between inflatable sections;

FIG. 2B shows cross sectional diagram of the embodiment illustrated in FIG. 2A with one inflatable section inflated;

DETAILED DESCRIPTION

Convective devices generally refer to a device distributing matter in gas state. For example, convective devices can receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. In some embodiments, a convective device has a pneumatic structure that is formed by two or more sheets and at least one of the sheets is air permeable that allows air distribution. At least some embodiments of the present disclosure direct to a convective device having at least two inflatable sections having a flow control device disposed between the two sections. In some embodiments, the flow control device is configured to remain closed when a first inflatable section is inflated but open when a second inflatable section is inflated. As used herein, "inflatable" refers to a structure which increases in volume when air or other gas is supplied at a pressure greater than atmospheric pressure to the interior of the structure. Typically these structures inflate at relatively low pressures such as pressures less than 100 mmHg, preferably at pressures less than 50 mmHg, more preferably at pressures less than 25 mmHg. Typically the volume of the inflatable section can increase by greater than 100%.

Figure 1A:
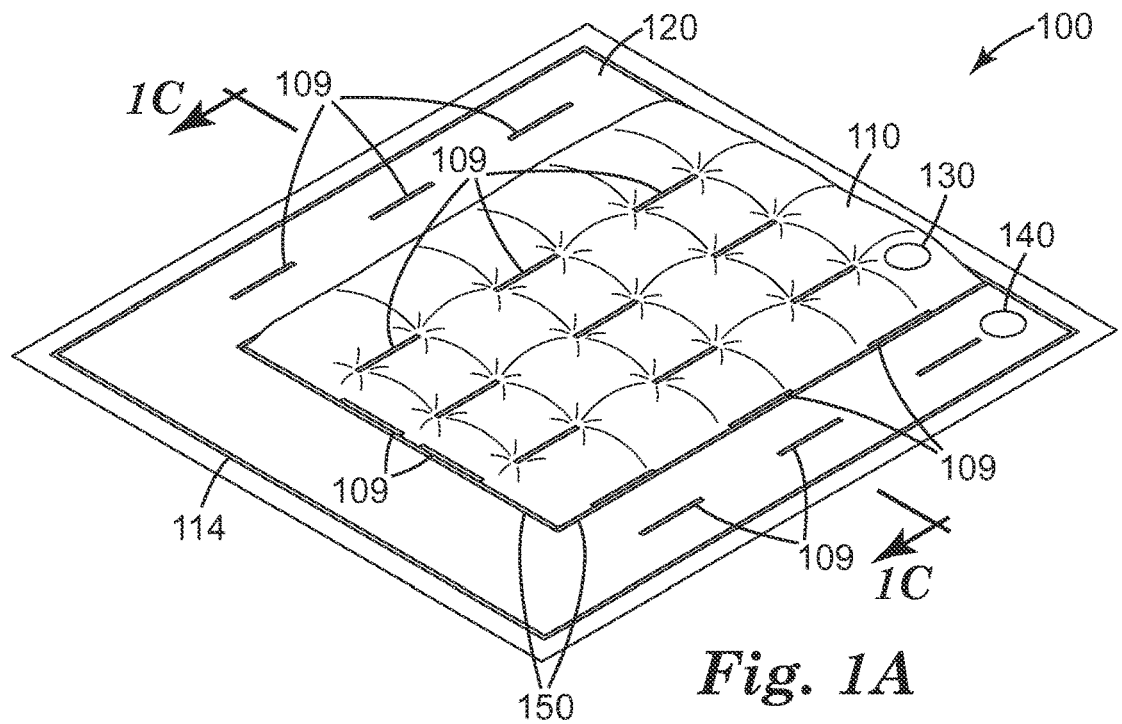
FIG. 1A shows a prospective view of an embodiment of a convective device having two inflatable sections with a flow control device between the sections.
Figure 1B:
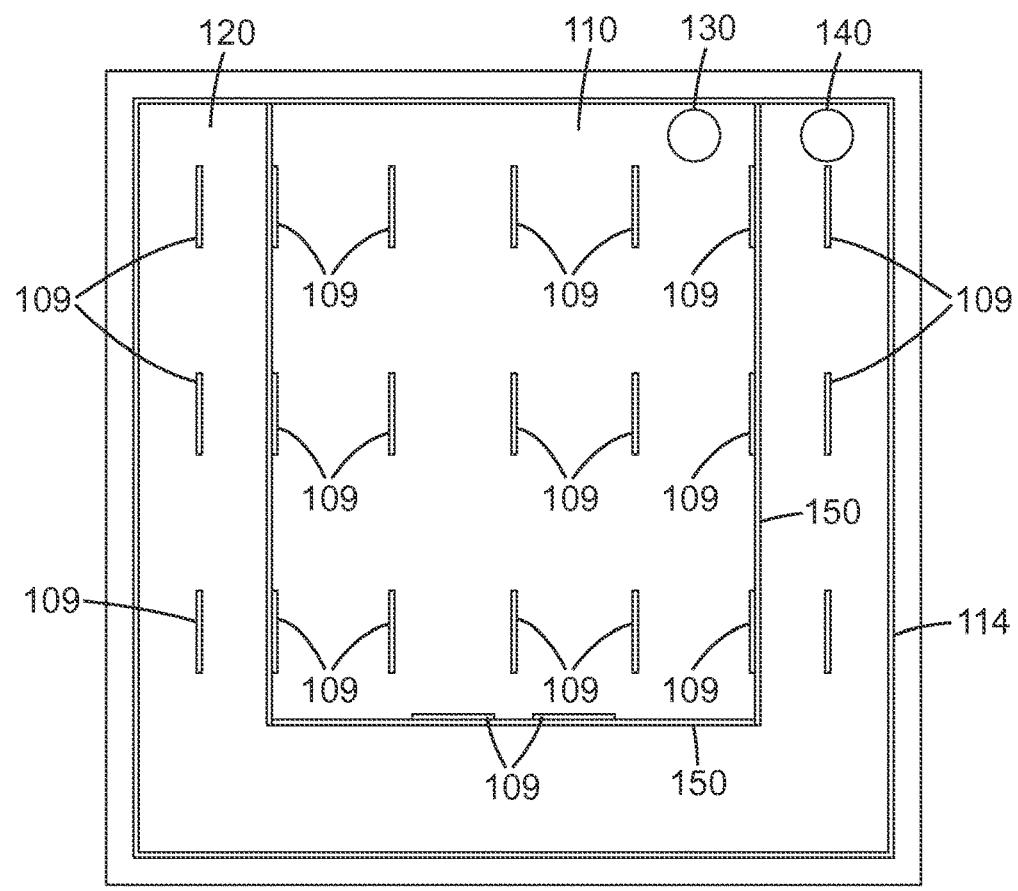
FIG. 1B is top plan view of the embodiment illustrated in FIG. 1A.

FIG. 1A shows a prospective view of an embodiment of a convective device 100 having two inflatable sections with a flow control device between the sections; FIG. 1B shows a top plane view of the embodiment illustrated in FIG. 1A; and FIG. 1C is a cross sectional view of the embodiment illustrated in FIG. 1A. In this embodiment, the convective device 100 has two inflatable sections 110 and 120, openings 130 and 140, and flow control device 150 between the inflatable sections 110 and 120. The flow control device 150 is elongated and disposed proximate the boundaries of the sections 110 and 120. In some cases, the flow control device 150 is opened when one section (e.g. section 120) is inflated but remains close when another section (e.g. section 110) is inflated. For example, the flow control device 150 is opened when section 110 is inflated by inflating medium 160 and the inflating medium can enter into section 120 through the flow control device 150 and inflate section 120. Conversely, the flow control device 150 remains closed when section 110 is inflated by inflating medium and section 120 can remain uninflated, as illustrated in FIGS. 1A and 1C.

Although two inflatable sections illustrated, a convective device may have more than two inflatable sections and more than one flow control device between two adjacent sections. In some cases, the flow control device 150 is configured to open when the inflatable section 120 is inflated with inflating medium having pressure greater than a predetermined threshold. In some cases, at least part of the flow control device can be formed by materials that are used in the inflatable sections. For example, an inflatable section is formed by two sheets and at least part of the flow control device is formed by one of sheets.

The opening 130 allows an inflating medium source (not illustrated) to connect and provide inflating medium to inflate the inflatable section 110. The opening 140 allows an inflating medium source (not illustrated) to connect and provide inflating medium to inflate the inflatable section 120. For example, the openings can include one or more inlet ports, cuffs, sleeve openings at the edge, or the like. The inflatable sections 110 and 120 can connect to the same inflating medium source or different inflating medium sources. In some cases, the sections 110 and 120 connect to two air sources each providing pressurized air at different pressures. For example, the air source connected to the section 120 provides pressurized air with higher pressure than the pressurized air provided to section 110. In some cases, the inflating medium is purified or filtered ambient air which is supplied from an air compressor/heater. In some cases, the opening 130 can have a different shape and/or size from the opening 140. In one embodiment, the opening 130 is configured to receive a hose nozzle of a first diameter or shape and the opening 140 is configured to receive a hose nozzle of a second diameter or shape different than the first diameter or shape.

In some embodiments, the convective device 100 can be generally planar in uninflated state. In some embodiments, the convective device 100 can have two layers 105 and 107, where the inflating medium can be provided to inflate the space between the two layers. In some cases, one of the two layers, for example, 105 is flexible. In some implementations, both layers 105 and 107 can be flexible. Each of the layers 105 and 107 can have one or more sheets of material, for example, a multilayer laminate sheet. In some embodiments, the flow control device 150 can be formed by one or more adhesive strips functioning together with heat seals to open when the inflating medium is flowing along one direction and remain close when the inflating medium 160 is flowing along another direction. In some other embodiments, the flow control device 150 can be formed by an air permeable strip and an air impermeable strip configured to cover the air permeable strip in a close state and uncover the air permeable strip in an open state. A flow control device is typically used between two or more inflatable sections. The two or more inflatable sections can have various position relationships, for example, adjacent, stacking, tangent, peripheral, surrounding, or the like. Different constructions of the flow control device 150 are described in further details hereinafter.

In some implementations, the first layer 105 and/or the second layer 107 includes an underside sheet formed from a flexible, fibrous, preferably non-woven structure composed of polymeric materials capable of bonding to an upper side sheet of a heat-sealable polymeric material. For example, the underside sheet may be a non-woven, hydroentangled polyester material and the upper side layer may include a polyolefin such as a polypropylene film which is extrusion-coated, thermally laminated, or adhesively laminated onto the polyester layer. Alternatively, the underside sheet may comprise a non-woven, paper-based material to which the upper side layer, including either a polyethylene or polypropylene film, has been glue laminated. In one embodiment, the upper side and underside sheets can be made with a stratum of absorbent tissue paper prelaminated with a layer of heat-sealable plastic.

In some embodiments, the second layer 107 includes the upper side sheet and the underside sheet, and the first layer 105 comprises the same material as the upper side sheet of the second layer 107. The first layer 105 thus may include a sheet of plastic bonded to the plastic upper side of the second layer 107. It is preferably attached by a continuously-running web process including stations that provide an interruptible heat-sealing process. This interruptible heat sealing process can be controlled to form elongated heat seals that define the inflatable channels therebetween. The seals can be formed as continuous air impervious seals or discontinuous air permeable seals. The interruptible heat sealing process can be used to form the continuous seams, one of which is the seam 114 at the peripheral of the second layer 107 and the first layer 105. In some cases, the interruptible heat sealing process can be used to form the discontinuous heat seals 109. In some cases, absorbent material can be applied to the convective device 100, for example, applied as a single material layer. The absorbent material can be bonded to the upper plastic layer by heat processing or by adhesive bonding.

In some embodiments, the convective device is enabled to bathe a patient in the thermally controlled inflating medium introduced into the convective device 100, when inflated, via an air permeable layer, 105 and/or 107. A layer can be air permeable using various materials or mechanical structures, for example, air-permeable materials, apertures, interstices, slits, or the like. In some implementations of an air permeable sheet with apertures, the density of apertures can vary among areas and/or inflatable sections. For example, the inflatable section 120 can have apertures with higher density than apertures in the inflatable section 110. The apertures comprise openings which can be of any appropriate shape and size. In some cases, an inflatable section can be constructed with two layers of materials different from another inflatable section. In some other cases, the two or more inflatable sections can be constructed with same materials.

In some embodiments, the first layer 105 and/or the second layer 107 are made from a polyolefin non-woven extrusion coated, each with a coating of polypropylene on one side. In some other embodiments, the first layer 105 and/or the second layer 107 can be poly lactic acid spunbond with polyolefin based extrusion coat. One of the first layer 105 and second layer 107 may have holes formed by punching, slitting, or cutting to permit the flow of pressurized inflating medium from the inflated section through the layer. In some cases, the holes can be opened through both layers 105 and 107. In some cases, when the convective device 100 is assembled, the polypropylene-coated side of the first layer 105 is sealed to the polypropylene-coated side of the second layer 107 at the periphery 114, and at the one or more locations 109 to form the construction. The sealing process can use various techniques, for example, ultrasonic welding, radio frequency welding, heat sealing, or the like. Alternatively, the first layer 105 and second layer 107 may each include a laminate of polypropylene and polyolefin web with holes formed in at least one of the layers to support passage of pressurized air. In yet another embodiment, at least one of the layers 105 and 107 can use air permeable material, for example, spunbond-meltblown-spunbond (SMS) nonwoven material, or the like.

Forced air warming is used for three distinct, but overlapping, clinical purposes: 1) establishing thermal comfort, 2) prewarming, and 3) restoring and maintaining normothermia. In the cases of establishing thermal comfort and prewarming, the subject may be unanesthetized; however, to restore and maintain normothermia, the subject can be either awake or anesthetized. Only the first and third purposes are therapeutic in the sense that they are restorative or salubrious. Prewarming, on the other hand, is not therapeutic in the strict sense because it is an intentional perturbation of the body's normal heat balance.

Convective devices can be used to effectively and safely administer a uniformly thermally-controlled bath of the inflating medium to a patient within space proximate the device. A convective device may create the conditions necessary to produce thermal comfort, or it may prevent heat loss from, or it may transfer heat into, a subject's body. Although, thermal comfort is a subjective notion, the environmental conditions necessary to produce a sense of thermal comfort in a population of human beings are known and well tabulated. For example, Fanger (Thermal Comfort: Analysis and Applications of Environmental Engineering. Danish Technical press, Copenhagen, 1970) defines thermal comfort as "that condition of mind which expresses satisfaction with the thermal environment." Even when a patient is normothermic, less-than-ideal environmental conditions, including non-uniform ambient temperature, can result in acute thermal discomfort, which is largely determined with reference to skin temperature, not core body temperature.

Therapeutic warming may be indicated during any one or more of the perioperative periods; however, prewarming can be performed only prior to the induction of anesthesia. For example, for a short operation for which no intraoperative warming is planned, a person may be warmed preoperatively to raise mean body temperature to a level higher than normal in order to store enough thermal energy to maintain normothermia following anesthetic redistribution. After surgery, it may be necessary to apply therapeutic warming in a recovery area to raise the core temperature to a normal value and maintain it there for a period of time while anesthesia wears off. Alternatively, for a long surgery in an arena with heating equipment available, a person may be warmed for comfort before surgery and warmed therapeutically during and after surgery.

Both therapeutic and non-therapeutic warming may be provided by convective devices such as convective thermal blankets that receive and distribute warmed, pressurized air and then expel the distributed air through one or more surfaces toward a patient in order to prevent or treat hypothermia in the patient. An example of use of such a device for therapeutic warming is found in U.S. Pat. No. 6,524,332, "System and Method for Warming a Person to Prevent or Treat Hypothermia", commonly owned with this application. The use of convective means to establish the conditions necessary for thermal comfort is described in the referenced U.S. Patent Application, and the referenced Publication No. WO 03/086500.

When delivered by convective devices, therapeutic warming is distinguished from non-therapeutic warming by intended effects and by the parameters of heat delivery that produce those effects. The important distinction here is whether the heat transfer produces an intentional perturbation of the established heat balance, in which case the purpose is non-therapeutic, such as occurs during prewarming. When the convective device is used to transfer heat into, or prevent the heat loss from, a subject, so as to restore a normal heat balance, the purpose is therapeutic. In this regard, a convective warming system typically includes a source of warmed pressurized air (also called a heater/blower unit, a forced air warming unit, a heater unit, etc.), a convective device such as a thermal blanket (which is, typically, inflatable), and a flexible conduit or air hose connecting the heater/blower unit with the thermal blanket. Use of such a system for a particular type of warming requires delivery of warmed air through a thermal blanket at parametric values that achieve a particular objective.

The conditions by which a convective device such as a thermal blanket produces conditions necessary to establish thermal comfort in normothermic individuals at steady state are significantly different from those necessary to treat hypothermia. Typically, the conditions for thermal comfort are met in a system with a relatively low capacity heater/blower unit, while those in a warming system designed for prewarming, intraoperative warming, or rewarming are achieved with a relatively high capacity heater/blower unit. The different capacities have led to the use of air hoses with different capacities, with those delivering air flow required to create the conditions for thermal comfort typically having smaller diameters than those required to restore or maintain normothermia. The result is a divergence of designs leading to installation of different air delivery infrastructures for each clinical purpose. Illustrative examples of convective devices are described in U.S. Pat. Nos. 7,276,076, 7,520,889, 7,749,261, and 7,871,428. Illustrative examples of heater/blower construction and operation are described in U.S. Pat. Nos. 6,876,884; 7,819,911; and 7,976,572.

FIG. 2A is a top view of one embodiment of a flow control device 200 between inflatable sections. The flow control device 200 is elongated and separates two inflatable sections 201 and 202. The flow control device 200 can include one or more adhesive and/or mechanical attachment means. In some cases, as illustrated in FIG. 2A, the flow control device 200 includes an elongated adhesive strip extending proximately the boundary between the two inflatable sections 201 and 202 from each other. The flow control device 200 typically have two states: an open state allowing the flow of inflating medium from one inflatable section to another; and a close state blocking the flow of inflating medium from one inflatable section to another. In some embodiments, the flow control device 200 operates as a one-way flow control device such that allowing inflating medium to flow through in one direction. The adhesive strip can be made from any releasable adhesive materials for example, pressure sensitive adhesive. In one embodiment, as illustrated in FIG. 2A, the flow control device 200 is disposed proximate a discontinuous heat seal 210, where the heat seal is closer to the inflatable section 202 than the inflatable section 201. The heat seal 210 is discontinued at locations 230. Such configuration allows the flow control device 200 to open when the section 201 is inflated and the inflating medium can flow in the direction of 220, through the locations 230. The flow control device 200 remains closed, however, when the section 202 is inflated, thus preventing the flow of inflating medium from section 202 to section 201.

FIG. 2B shows cross sectional diagram of the embodiment illustrated in FIG. 2A with the inflatable section 201 inflated. The inflatable section 201 includes a first layer 215 and a second layer 217. The inflatable section 202, in this embodiment, also includes the first layer 215 and the second layer 217. When the section 201 is inflated, the flow control device 200 is pulled open by the inflating medium in the direction of 225B and 226B, which are generally in a direction perpendicular to the surface orientation of the flow control device 200. As illustrated, the flow control device 200 is open and allows the inflating medium to go through at the locations where the heat seal 210 is not present, for example, at locations 230. In the embodiment as illustrated, the flow control device 200 is disposed on both the first layer 215 and the second layer 217. In an alternative embodiment, the flow control device 200 can be disposed on one of the layers 215 and 217. In yet another embodiment, the flow control device 200 can be a discontinuous adhesive strip.

Figure 2C:
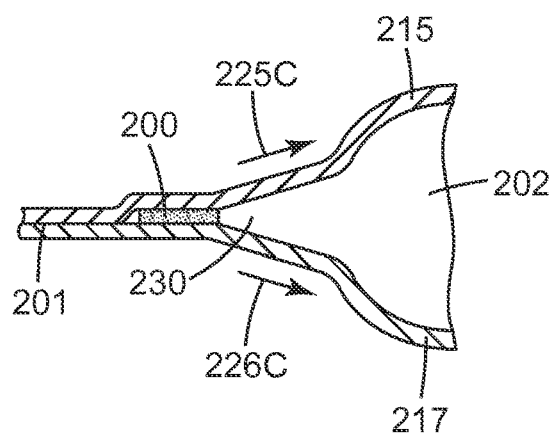
FIG. 2C shows cross sectional diagram of the embodiment illustrated in FIG. 2A with another inflatable section is inflated.

FIG. 2C shows cross sectional diagram of the embodiment illustrated in FIG. 2A with the inflatable section 202 is inflated. At the locations that the heat seal 210 is disposed between the inflatable section 202 and the flow control device 200, the flow control device 200 will not receive any pulling force from the inflating medium. At the locations 230 where the heat seal is not disposed, the inflating medium is pulling the flow control device at the directions of 225C and 226C, which are at angles less than 90° from the surface orientation of the flow control device 200. In this case, the flow control device is less likely to be pulled open and can remain closed.

Figure 2D:
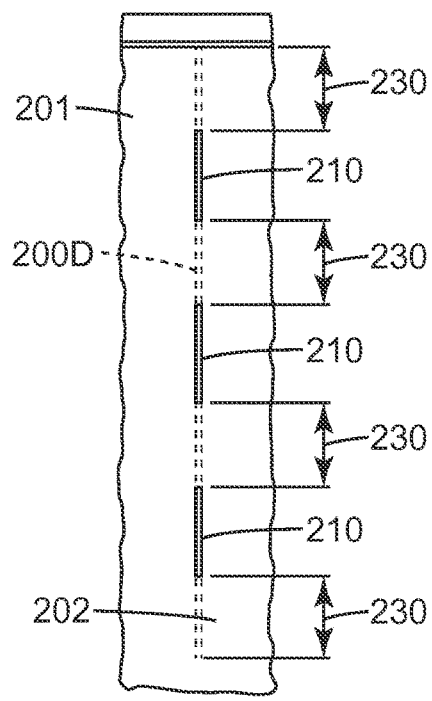
FIG. 2D is a top view of another embodiment of a flow control device.

In some cases, as illustrated in FIG. 2D, a flow control device 200D can be disposed between the discontinued heat seals 210. In such embodiment, the flow control device 200D can be opened when the pressure of the inflating medium is greater than a predetermined threshold. Thus, the flow control device 200D can remain close when the pressure of the inflating medium is lower than the predetermined threshold. For example, the predetermined pressure threshold is 50 mmHg, the section 202 is inflated with air at the pressure of 30 mmHg, so the flow control device 200D remains closed and the section 202 is inflated but the section 201 is uninflated. Using the same example, when the section 202 is inflated with air at the pressure of 60 mmHg, the flow control device 200D is opened such that both the sections 201 and 202 are inflated with the air going through the flow control device 200D.

Figure 3A:
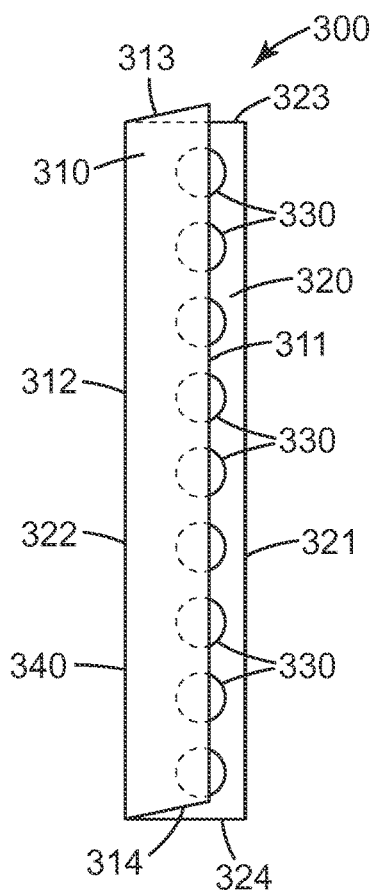
FIG. 3A is a close-up view of another embodiment of a flow control device.

FIG. 3A is a close-up view of another embodiment of a flow control device 300, which can be used between inflatable sections. The flow control device 300 includes an elongated air impermeable strip 310 and an elongated air permeable strip 320. An air impermeable strip refers to a strip with less air permeability than the air permeability of an air permeable strip. The air permeability of an air impermeable strip is, for example, 5% of the air permeability of an air permeable strip. In some other examples, the air permeability of an air impermeable strip is 10%, 20%, 30%, 40%, or 50% of the air permeability of an air permeable strip. Air permeability can be measured cubic centimeters per minute or cubic feet per minute. The air impermeable strip 310 has a first edge 311, a second edge 312, a first end 313, and a second end 314. The air permeable strip 320 has a first edge 321, a second edge 322, a first end 323, and a second end 324. The second side 312 of the air impermeable strip 310 is proximate the second side 322 of the air permeable strip 320 at a line 340. In some embodiments, the air impermeable strip 310 covers the air permeable strip 320 when the flow control device 300 is in a close state not allowing air to go through. The air impermeable strip 310 does not cover the air permeable strip 320 when the flow control device 300 is in an open state allowing air to go through. In the open state, the first side 311 of the air impermeable strip 310 has some distance from the first side 321 of the air permeable strip 320.

The air permeable strip 320 can include openings 330, for example, apertures, slits, holes, or the like. In some cases, at least sections of the air permeable strip 320 can be made using air permeable materials. Air permeable materials include, for example, woven fabrics, nonwoven fabrics, perforated film, porous film, laminated material (e.g. nonwoven fabrics with perforated film, etc.), flocked fabrics, and the like. Nonwoven fabrics include, for example, carded thermally bonded nonwovens, spunbond nonwovens, hydroentangled/spunlaced nonwovens, SMS (Spunbond-Meltblown-Spunbond) nonwovens, airlaid nonwovens, wet-laid nonwovens, or the like. The air impermeable strip 310 uses materials having less air permeability (i.e., air impermeable materials). Air impermeable materials include, for example, single layer plastic film (e.g., Polyethylene, Propylene, Polyurethane, polyester, etc.), metal film (e.g., aluminum foil film, etc.), elastic film (e.g., polyurethane, Kratons, etc.), multi-layer film (e.g., co-extruded film, blown film, etc.), film coated paper, and the like.

Figure 3B:
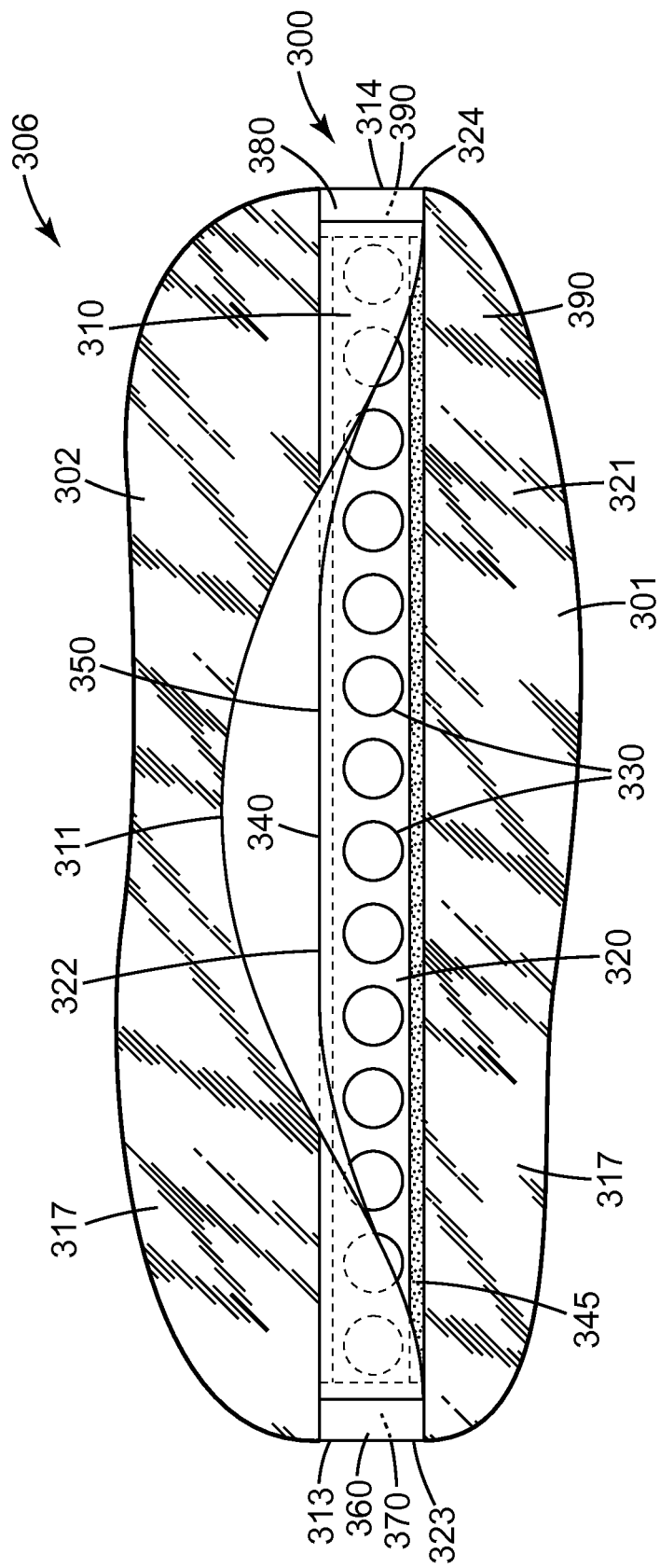
FIG. 3B illustrates a prospective view of the application of the flow control device illustrated in FIG. 3A.

FIG. 3B illustrates a prospective view of the application of the flow control device 300 illustrated in FIG. 3A in a convective device 306, when the flow control device 300 is in the open state and the top layer is removed. The flow control device 300 is disposed between the inflatable section 301 and the inflatable section 302 of the convective device 306. In this embodiment, the convective device 306 includes a first layer 315, which is removed from this view, and a second layer 317, which form both of the inflatable sections 301 and 302.

In some embodiments, an attachment device 345 is applied proximate to the first side 321 of the air permeable strip 320 and an attachment device 350 is applied proximate to the second side 322 of the air permeable strip 320. The attachment device 345 and the attachment device 350 can use any attachment means, for example, adhesive, perforated tear-away tabs, hook and loop, sewing, snaps, heat, ultrasonic weld, rivets, mechanical flow control devices, or the like. In some cases, the attachment devices 345 and/or 350 can use continuous adhesive strips. In some other cases, the attachment devices 345 and/or 350 can have patterned adhesive areas, where one or more adhesive areas may include adhesives of various properties and compositions. In the embodiment illustrated in FIG. 3B, the first attachment device 345 is attached to the first layer 315 (not shown) and the second attachment device 350 is attached to the second layer 317.

In some implementations, the air impermeable strip 310 and the air permeable strip 320 can be formed by two strips of one sheet of material folded along a line 340, thus the second side 312 of the air impermeable strip 310 and the second side 322 of the air permeable strip 320 are the same line as the line 340. In such implementations, the air permeable strip 320 can include mechanical structures to allow air to go through, for example, apertures, holes, slits, openings of any shape, or the like. In some cases, the air impermeable strip 310 includes a section 360 proximate to the first end 313 attached to a section 370 proximate to the first end 323 of the air permeable strip 320 to facilitate the flow control device 300 to change between open state and close state. In some other cases, the air impermeable strip 310 also includes a section 380 proximate to the second end 314 attached to a section 390 proximate to the section end 324 of the air permeable strip 320.

Figure 3C:
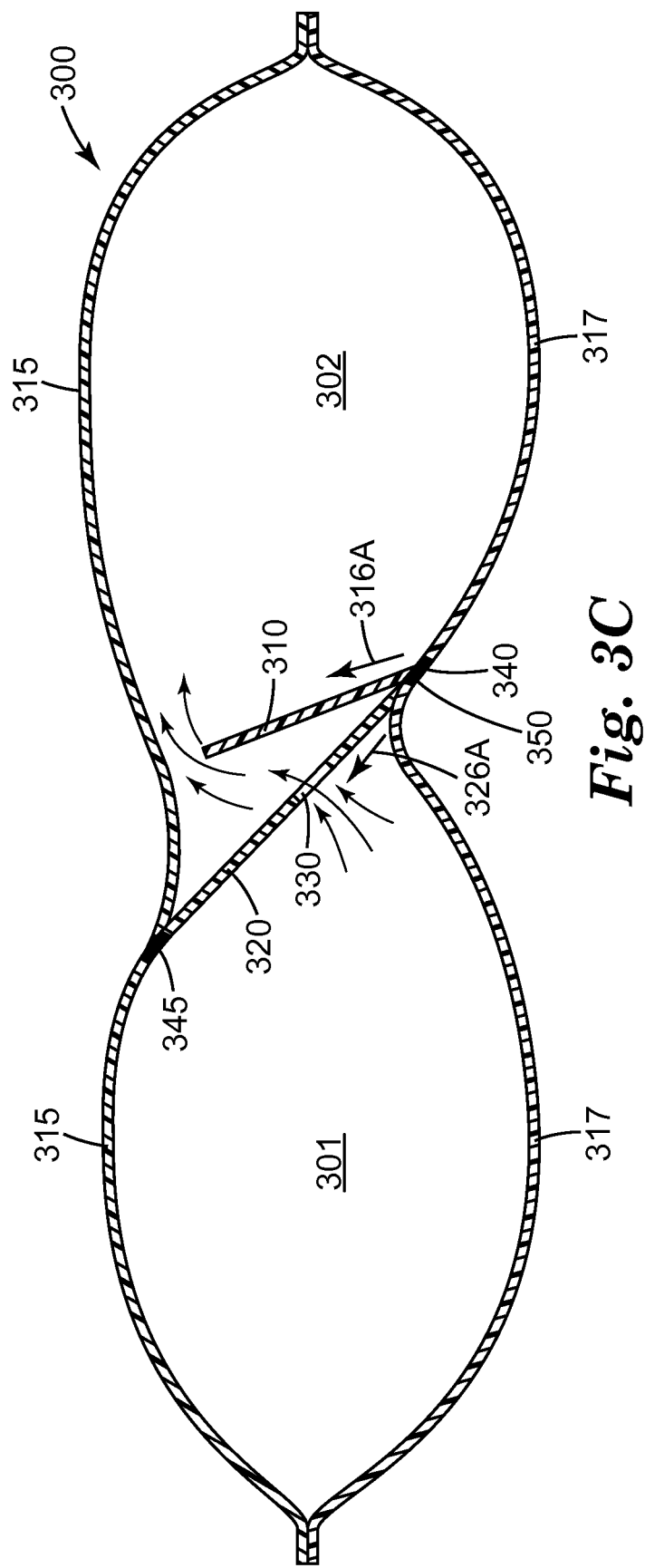
FIG. 3C is a cross-sectional schema diagram of the flow control device in the open state.

FIG. 3C is a cross-sectional schema diagram of the flow control device 300 in the open state. When section 301 is inflated, the first layer 315 and the second layer 317 are separated in section 301 and inflating medium hits the air permeable strip 320 such that the air permeable strip 320 is separated from the air impermeable strip 310. The air permeable strip 320 is extended from the line 340 at a direction 326A and the air impermeable strip 310 is extended from the line 340 at a direction 316A. In the open state, the direction 316A is diverged from the direction 326A.

Figure 3D:
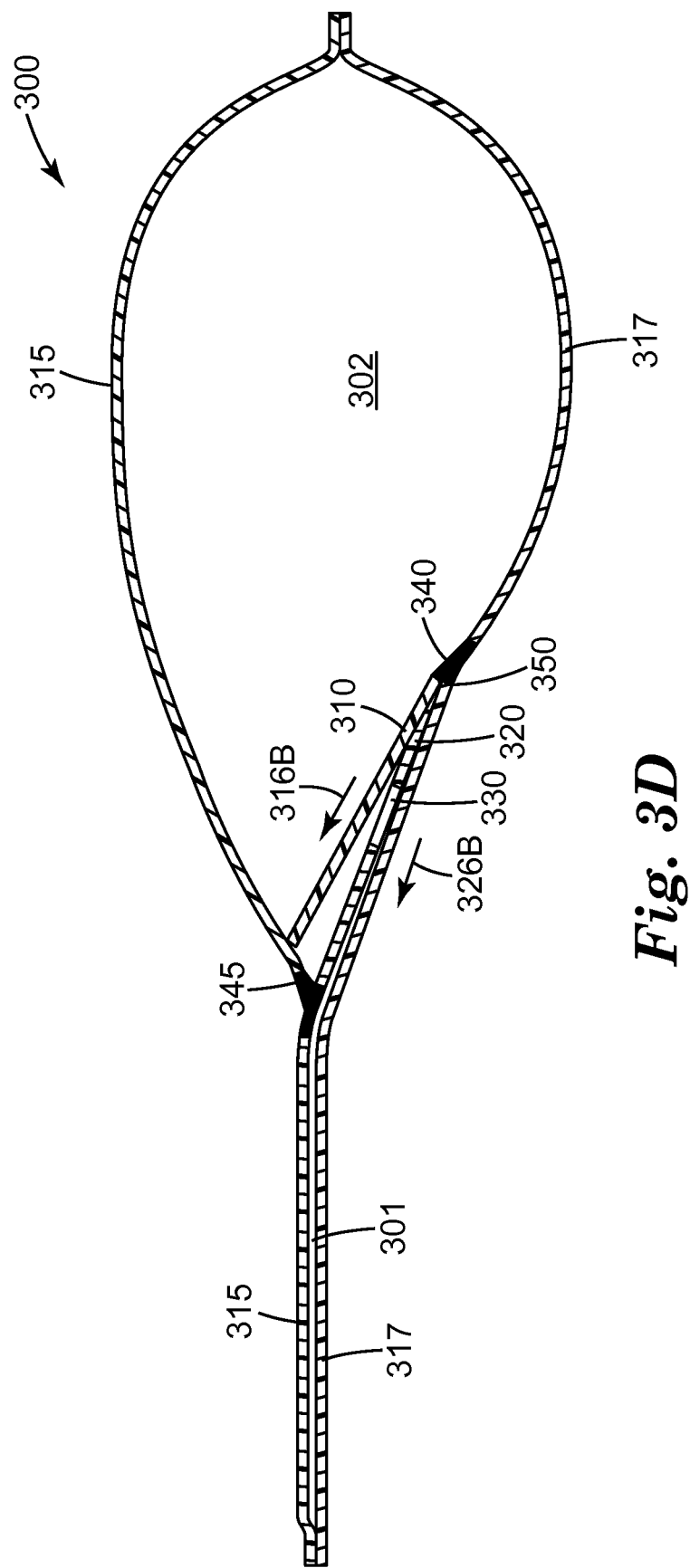
FIG. 3D is a cross-sectional schema diagram of the flow control device in the close state.

FIG. 3D illustrates a cross-sectional schema diagram of the flow control device 300 in the closed state. When section 302 is inflated, the first layer 315 and the second layer 317 are separated in section 302 and inflating medium hits the air impermeable strip 310 such that the air impermeable strip 310 is pushed toward the air permeable strip 320. The air permeable strip 320 is extended from the line 340 at a direction 326B and the air impermeable strip 310 is extended from the line 340 at a direction 316B. In the close state, the direction 316B is proximately the same as the direction 326B. The inflating medium is blocked by the air impermeable strip 310 and cannot enter into section 301, so the flow control device 300 remains close.

Figure 4A:
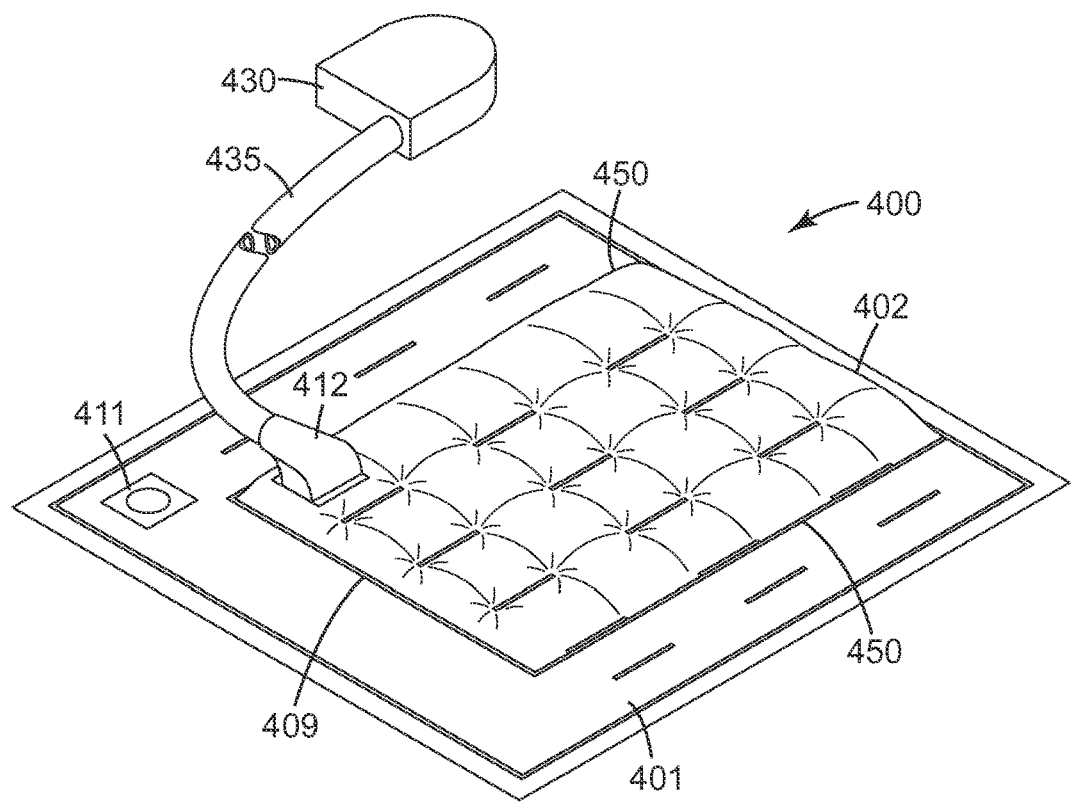
FIG. 4A and FIG. 4B illustrate an exemplary embodiment of a convective device using a one-way flow control device.
Figure 4B:
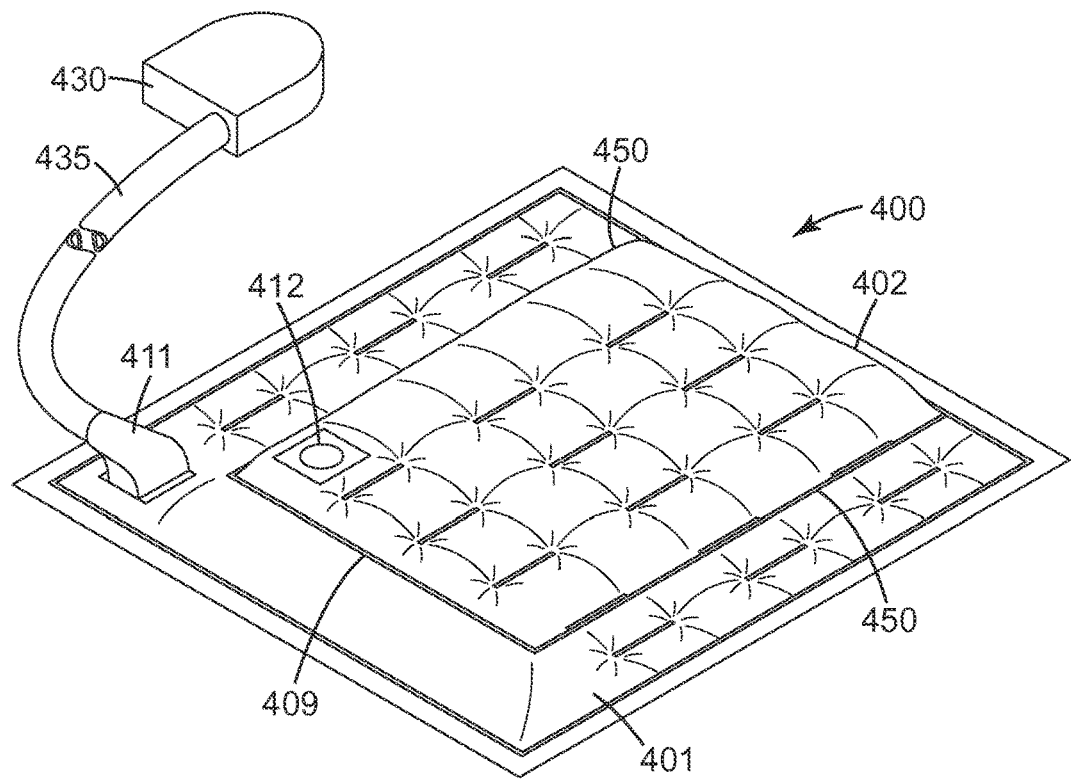

FIG. 4A and FIG. 4B illustrate an exemplary embodiment of a convective device 400 using a one-way flow control device 450. The convective device 400 has an inflatable section 401 and an inflatable section 402. A one-way flow control device 450 is used between the inflatable sections 401 and 402. The one-way flow control device 450 can use any of the embodiments described above. In the embodiment as illustrated, a heat seal 409 can be disposed at a part of the boundary between the inflatable sections 401 and 402.

The inflatable section 401 has an inlet port 411 and the inflatable section 402 has an inlet port 412. An air source 430 provides pressurized air via an air hose 435 coupled to the inlet port 412 to the inflatable section 402. The flow control device 450 remains closed such that the inflatable section 401 remains uninflated. FIG. 4B illustrates an air source 430 provides pressurized air through the air hose 435 coupled to the inlet port 411 to the inflatable section 401. The flow control device 450 is opened such that the inflatable section 402 is also inflated.

EXEMPLARY EMBODIMENTS

Embodiment 1

A convective device, comprising:
a first inflatable section having a first opening,
a second inflatable section having a second opening, and
a flow control device disposed between the first inflatable section and the second inflatable section, the flow control device configured to open when the second inflatable section is inflated with inflating medium and remain closed when the first inflatable section is inflated with inflating medium.

Embodiment 2

The convective device of Embodiment 1, wherein the flow control device comprises a releasable adhesive strip.

Embodiment 3

The convective device of Embodiment 1 or Embodiment 2, wherein the flow control device comprises an air permeable strip and an air impermeable strip.

Embodiment 4

The convective device of any one of Embodiment 1 through Embodiment 3, wherein the first opening is configured to receive a hose nozzle of a first size and the second opening is configured to receive a hose nozzle of a second size different than the first size.

Embodiment 5

The convective device of any one of Embodiment 1 through Embodiment 4, wherein the first opening is configured to receive a hose nozzle of a first shape and the second opening is configured to receive a hose nozzle of a second shape different than the first shape.

Embodiment 6

The convective device of any one of Embodiment 1 through Embodiment 5, wherein the flow control device is configured to open when the second inflatable section is inflated with inflating medium having pressure greater than a predetermined threshold.

Embodiment 7

The convective device of any one of Embodiment 1 through Embodiment 6, further comprising:
a seal between the first inflatable section and the second inflatable section, wherein at least part of the flow control device is adjacent to the seal.

Embodiment 8

The convective device of Embodiment 7, wherein the seal has a first side facing to the first inflatable section and a second side facing to the second inflatable section, wherein the at least part of the flow control device is adjacent to the second side of the seal.

Embodiment 9

The convective device of any one of Embodiment 1 through Embodiment 8, wherein the flow control device comprises an elongated adhesive strip.

Embodiment 10

A flow control device, comprising:
an air permeable strip having a first side, a second side, a first end, and a second end,
an air impermeable strip having a first side, a second side, a first end, and a second end, the second side of the air impermeable strip being proximate the second side of the air permeable strip, the air impermeable strip configured to cover the air permeable strip in a close state of the flow control device and uncover the air permeable strip in a open state of the flow control device.

Embodiment 11

The flow control device of Embodiment 10, wherein the air permeable strip is attached to the air impermeable strip proximate to the first end of the air permeable strip and the first end of the air impermeable strip.

Embodiment 12

The flow control device of Embodiment 10 or Embodiment 11, wherein the first side of the air impermeable strip is proximate to the first side of the air permeable strip in the close state of the flow control device.

Embodiment 13

The flow control device of any one of Embodiment 10 through Embodiment 12, wherein the air permeable strip and the air impermeable strip are formed by a sheet of air impermeable material folded and the air permeable strip includes one or more openings allowing inflating medium to go through.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices and materials falling within the spirit and scope of the invention as defined by the appended claims.

What is claimed is:
1. A convective device, comprising:
a first inflatable section having a first opening,
a second inflatable section having a second opening, and
a flow control device disposed between the first inflatable section and the second inflatable section, the flow control device configured to open when the second inflatable section is inflated with inflating medium and remain closed when the first inflatable section is inflated with inflating medium, wherein an inlet pressure at the first opening or the second opening is less than 100 mmHg when inflated and a volume of the first inflatable section or the second inflatable section increases by greater than 100% when inflated.

2. The convective device of claim 1, wherein the flow control device comprises a releasable adhesive strip.

3. The convective device of claim 1, wherein the flow control device comprises an air permeable strip and an air impermeable strip.

4. The convective device of claim 1, wherein the first opening is configured to receive a hose nozzle of a first size and the second opening is configured to receive a hose nozzle of a second size different than the first size.

5. The convective device of claim 1, wherein the first opening is configured to receive a hose nozzle of a first shape and the second opening is configured to receive a hose nozzle of a second shape different than the first shape.

6. The convective device of claim 1, wherein the flow control device is configured to open when the second inflatable section is inflated with inflating medium having pressure greater than a predetermined threshold.

7. The convective device of claim 1, further comprising:
a seal between the first inflatable section and the second inflatable section, wherein at least part of the flow control device is adjacent to the seal.

8. The convective device of claim 7, wherein the seal has a first side facing to the first inflatable section and a second side facing to the second inflatable section, wherein the at least part of the flow control device is adjacent to the second side of the seal.

9. The convective device of claim 1, wherein the flow control device comprises an elongated adhesive strip.

10. A convective device, comprising:
a first inflatable section having a first opening,
a second inflatable section having a second opening, and
a flow control device disposed between the first inflatable section and the second inflatable section, the flow control device configured to open when the second inflatable section is inflated with inflating medium and remain closed when the first inflatable section is inflated with inflating medium, wherein the flow control device comprises a releasable adhesive strip.

11. The convective device of claim 10, wherein the flow control device comprises an air permeable strip and an air impermeable strip.

12. The convective device of claim 10, wherein the first opening is configured to receive a hose nozzle of a first size and the second opening is configured to receive a hose nozzle of a second size different than the first size.

13. The convective device of claim 10, wherein the flow control device is configured to open when the second inflatable section is inflated with inflating medium having pressure greater than a predetermined threshold.

14. The convective device of claim 10, further comprising:
a seal between the first inflatable section and the second inflatable section, wherein at least part of the flow control device is adjacent to the seal.

15. The convective device of claim 10, wherein the flow control device comprises an elongated adhesive strip.

* * * * *